(12) United States Patent
Kasper et al.

(10) Patent No.: US 6,399,077 B1
(45) Date of Patent: Jun. 4, 2002

(54) METHOD OF AUGMENTING T CELL-MEDIATED IMMUNITY AGAINST TOXOPLASMA GONDII

(75) Inventors: Lloyd H. Kasper, Norwich, VT (US); Imtiaz A. Khan, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 09/230,914

(22) PCT Filed: Aug. 7, 1997

(86) PCT No.: PCT/US97/13917

§ 371 (c)(1),
(2), (4) Date: May 19, 1999

(87) PCT Pub. No.: WO98/06434

PCT Pub. Date: Feb. 19, 1998

Related U.S. Application Data

(60) Provisional application No. 60/023,489, filed on Aug. 9, 1996.

(51) Int. Cl.$^7$ .............................................. A61K 39/012
(52) U.S. Cl. .................. 424/273.1; 424/85.1; 424/85.2; 424/265.1
(58) Field of Search ............................. 424/85.2, 234.1, 424/273.1, 184.1, 85.1, 265.1

(56) References Cited

U.S. PATENT DOCUMENTS 4,564,592 A * 1/1986 Gaafar et al. .................. 435/68

OTHER PUBLICATIONS

Doherty et al. (Journal of Immunology, vol. 156 No. 2, Jan. 1996, pp. 735–741).*

Brown et al., "MHC Genes and CD8$^+$T Cells Determine Cyst Number in *Toxoplasma gondii* Infection$^1$", 1990 *J. Immunol.* 145:3438.

Carson et al., "Interleukin (IL) 15 Is a Novel Cytokine That Activates Human Natural Killer Cells via Components of the IL–2 Receptor", 1994 *J. Exp. Med.*, 180:1395.

Carson et al., "Endogenous Production of Interleukin 15 by Activated Human Monocytes Is Critical for Optimal Production of Interferon–y by Natural Killer Cells In Vitro", 1995 *J. Clin. Invest.*, 96:2578.

Denkers et al., "Bone Marrow Macrophages Process Exogenous *Toxoplasma gondii* Polypeptides for Recognition by parasite–Specific Cytolytic T Lymphocytes", 1993 *J. Immunol.*, 150:517.

Gamero et al., Interleukin 15 Induction of Lymphokine–activated Killer Cell Function against 1995 *Cancer Res.*, 55:4988.

Gazzinelli et al., "Interleukin 12 is required for the T–lymphocyte–independent induction of interferon γ by an intracellular parasite and induces resistance in T–cell–deficient hosts", 1993 *Proc. Natl. Acad. Sci. USA*, 90:6115.

Gazzinelli et al., "Synergistic Role of CD4$^+$T Lymphocytes in IFN–γ Production and Protective Immunity Induced by An Attenuated *Toxoplasma gondii* Vaccine", 1991 *J. Immunol.*, 146:286.

Gazzinelli et al., Parasite–Induced IL–12 Stimulates Early IFN–γ Synthesis and Resistance During Acute Infection with *Toxoplasma gondii* ', 1994 *J. Immunol.*, 153:2533.

Grabstein et al., "Cloning of a T Cell Growth Factor That Interacts with the β Chain of the Interleukin–2 Receptor", 1994 *Science*, 264:965.

Hunter et al., "Studies on the role of interleukin–12 in acute murine toxoplasmosis", 1995 *Immunology*, 84:16.

Kasper et al., "Antigen–Specific (p30) Mouse CD8$^+$T Cells Are Cytotoxic Against *Toxoplasma gondii*–Infected peritoneal Macrophages$^1$", 1992 *J. Immunol.*, 148:1493.

Kasper et al., "IL–7 Stimulates Protective Immunity in Mice Against the Intracellular Pathogen, *Toxoplasma gondii*$^1$", 1995 *J. Immunol.*, 155:4798.

Khan et al., "Induction of Antigen–Specific Parasiticidal Cytotoxic T Cell Splenocytes by a Major Membrane Protein (P30) of *Toxoplasma gondii*$^1$", 1988 *J. Immunol.*, 141:3600.

Khan et al., "Induction of Antigen–specific human Cytotoxic T cells by *Toxoplasma gondii*", 1990 *J. Clin. Invest.*, 85:1879.

Khan et al., "Interleukin–12 Enhances Murine Survival against Acute Toxoplasmosis", 1994 *Infec. Immun.*, 62:1639.

Khan et al., "Antigen–Specific CD8$^+$T Cell Clone Protects Against Acute *Toxoplasma gondii* Infection in Mice$^1$", 1994 *J. Immunol.*, 152:1856.

Lau et al., "Cytotoxic T–cell memory without antigen", 1994 *Nature*, 369:648.

Nishimura et al., "IL–15 Is a Novel Growth Factor for Murine γδ T Cells Induced by Salmonella Infection $^1$", 1996 *J. Immunol.*, 156:663.

Seder et al., "Interleukin 12 acts directly on CD4+cells to enhance priming for interferon γ production and diminshes interleukin 4 inhibition of such priming", 1993 *Proc. Natl. Acad. Sci. USA*, 90:10188.

Seder et al., "Cytokine Interactions in Human Immunodeficiency Virus–infected Individuals:Roles of Interleukin (IL)–2, IL–12, and IL–15", 1995 *J. Exp. Med.*, 182:1067.

Subauste et al., "Murine CD8$^+$Cytotoxic T Lymphocytes Lyse *Toxoplasma gondii*–Infected Cells$^1$", 1991 *J. Immunol.*, 147:3955.

Sharma et al., "In Vivo Recombinant Interleukin 2 Administration Enhances Survival Against A Lethal Challenge with *Toxoplasma gondii*$^1$", 1985 J. Immunol 135: 4160–4163.

* cited by examiner

*Primary Examiner*—Donna C. Wortman
*Assistant Examiner*—Robert A. Zeman
(74) *Attorney, Agent, or Firm*—Licata & Tyrrell P.C.

(57) ABSTRACT

A method of augmenting T cell-mediated immunity against *Toxoplasma gondii* is provided. Immunization with *Toxoplasma gondii* soluble parasite antigen and exogenous rIL-15 was found to protect against *Toxoplasma gondii* infection.

2 Claims, 6 Drawing Sheets

METHOD OF AUGMENTING T CELL-MEDIATED IMMUNITY AGAINST TOXOPLASMA GONDII

This application is the National Stage of International Application No. PCT/US97/13917, filed Aug. 7, 1997, which claims the benefit of priority from U.S. application Ser. No. 60/023,489, filed Aug. 9, 1996.

INTRODUCTION

This invention was made in the course of research sponsored by the National Institutes of Health. The U.S. Government may have certain rights in this invention.

BACKGROUND OF THE INVENTION

The role of immune cytokines in determining the outcome of intracellular infection has become more evident. In mice, *Toxoplasma gondii* infection stimulates the production of IFN-γ, which is the principal mediator of protection against acute and chronic recrudescent infection. Of the ILs studied, IL-12 appears to be an essential cytokine for stimulating a protective host response (Gazzinelli et al., 1994 *J. Immunol.*, 153:2533; Khan et al., 1994 *Infec. Immun.*, 62:1639; Hunter et al., 1995 *Immunology*, 84:16). It has been reported that administration of exogenous IL-12 to immunocompetent or SCID mice (Gazzinelli et al., 1993 *Proc. Natl. Acad. Sci. USA*, 90:6115) protects against subsequent parasite challenge. Both macrophages and $CD4^+$ T cells produce IL-12 that, in turn, stimulates the proliferation of NK cells and $CD8^+$ cytotoxic T cells (Seder et al., 1993 *Proc. Natl. Acad. Sci. USA*, 90:10188). The role of IL-2 in host protective immunity to Toxoplasma infection is less clear. In mice, administration of exogenous IL-2 can protect against parasite challenge (Sharma et al., 1985 J. Immunol.) 155:4798. The mechanism for this partial protection may be due to an increase in the proliferation of NK cells. It was recently reported that IL-7 can protect against acute Toxoplasma infection (Kasper et al., 1995 *J. Immunol.*, 155:4798). Protection is most evident when IL-7 is administered early and continued throughout the course of infection. The principal T cell subset that mediates protection by IL-7 consists of $CD8^+$ cells. In vitro, these T cells produce IFN-γ and exhibit enhanced TL activity against macrophages infected with *T. gondii*.

IL-15 is a recently identified cytokine that is abundantly expressed by a wide variety of tissues and activated monocyte/macrophages (Grabstein et al., 1994 *Science*, 264:965). The gene for this cytokine has now been isolated from simian kidney epithelial cells (Grabstein, supra). Although the sequence of IL-15 is not homologous with that of IL-2, IL-15 uses components of the IL-2R for bonding and signal transduction (Carson et al., 1994 *J. Exp. Med.*, 180:1395). IL-15 is also a potent growth factor for activated T cells, and it enhances the cytolytic function of both NK and effector T cells. IL-15 appears to enhance LAK cell activity against certain tumors (Gamero et al., 1995 *Cancer Res.*, 55:4988). Although limited information is available on the role of IL-15 in response to infection, recent studies indicate that it stimulates the proliferation it T cells induced by Salmonella infection (Nishimura et al., 1996 *J. Immunol.*, 156:663) and may have a role in the host response to HIV infection (Seder et al., 1995 *J. Exp. Med.*, 182:1067). Endogenous production of IL-15 has now been observed to be important for optimal production of IFN-γ T by NK cells in vitro (Carson et al., 1995 *J. Clin. Invest.*, 96:2578).

It has now been found that mice immunized with *Toxoplasma gondii* soluble parasite Ag (TLA) and exogenous rIL-15 are protected against lethal Toxoplasma infection. Immunization increases the production IFN-γ and Ag-specific $CD8^+$ T cell proliferation. Adoptive transfer of these $CD8^+$ T cells into a naive host are protective against a lethal *T. gondii* challenge.

SUMMARY OF THE INVENTION

Cytokines of the Th1 profile are important mediators of protective host immunity against *Toxoplasma gondii* infection in mice. It has now been found that administration of exogenous rIL-15 with soluble Toxoplasma lysate Ag (TLA) provides complete protection against a lethal parasite challenge, whereas treatment with either rIL-15 or TLA alone is not protective. Following immunization with TLA/rIL-15, there is a significant proliferation of splenocytes expressing the $CD8^+$ phenotype in response to TLA. A significant rise in the level of serum IFNγ was observed in vaccinated mice. Adoptive transfer of $CD8^+$ T cells, but not $CD4^+$ T cells, from TLA/rIL-15-vaccinated mice protects naive mice from a lethal parasite challenge. These $CD8^+$ T cells exhibit enhanced CTL activity against target macrophages infected with *T. gondii*. Mice that have been immunized are protected against lethal parasite challenge for at least 1 month postvaccination. These results demonstrate that TLA when administered with exogenous rIL-15 generates toxoplasmacidal Ag-specific $CD8^+$ cells. These T cells proliferate upon exposure to parasite Ag, exhibit long term memory CTL against infected target cells, and may be involved in host immune memory to this parasite. Accordingly, a novel method of augmenting T cell-mediated immunity against *Toxoplasma gondii* is provided.

DETAILED DESCRIPTION OF THE INVENTION

Figures 1, 2:
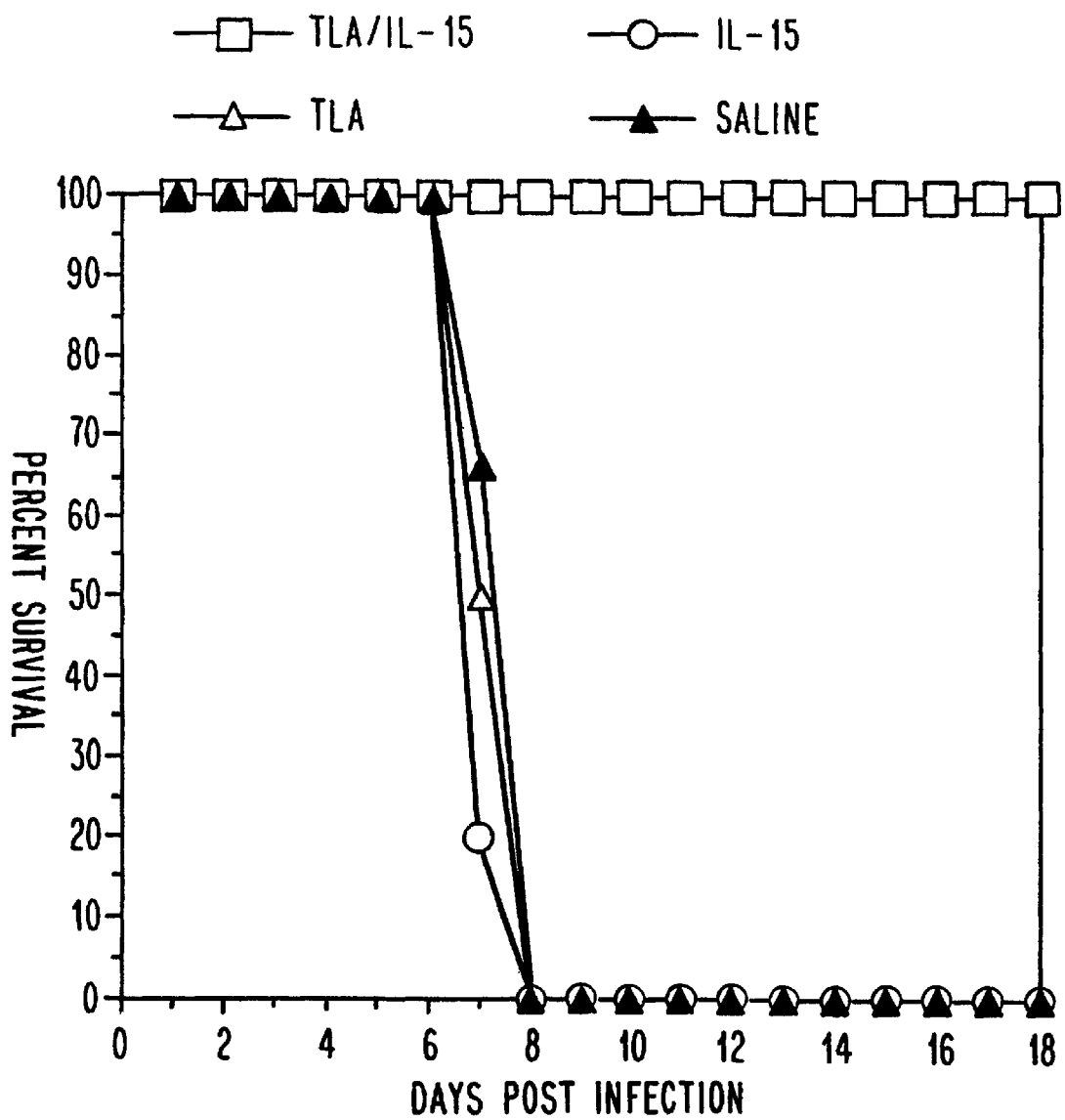
FIG. 1 is a diagram of the vaccination protocol for administration of rIL-15 and soluble TLA to mice. Mice were immunized with rIL-15 (15 μg/day) and TLA (5 μg/) via i.p. inoculation.
FIG. 2 is a graph showing that rIL-15 in combination with soluble tLA protects mice against parasite challenge. Inbred BALB/c mice (n=6/group) were immunized with TLA in combination with IL-15 as described in FIG. 1. Controls received an equivalent amount of IL-15 alone, TLA, or saline. One week after the booster dose, the mice were challenged with $1\times10^4$ parasites by I.P. inoculation. The data are representative of two experiments.

Exogenous rIL-15, when administered with a soluble parasite Ag, protects against acute Toxoplasma infection. The protective response elicited by vaccination with TLA/rIL-15 can be observed for at least 1 month postimmunization. The protective response appears to be mediated in part by the induction of Ag-specific $CD8^+$ T cells. These $CD8^+$ T cells are cytolytic for at least one month postvaccination against macrophages infected with *T. gondii*. These observations indicate that IL-15 may play an important role in the induction of long term $CD8^+$ T cell immunity against this parasite.

IL-15 is a recently described cytokine produced by a wide range of cells that stimulates the proliferation of immune cells. Recent observations have demonstrated that IL-15 can increase the proliferation of PBMC from HIV-infected individuals in response to HIV-specific Ag (Seder et al., 1995 *J. Exp. Med.*, 182:1067). When administered with soluble parasite Ag, rIL-15 is able to sensitize splenocytes to proliferate in response to the parasite Ag in vitro. A marked increase in splenocyte proliferation was observed in mice vaccinated with TLA/rIL-15, compared with that in mice vaccinated with either TLA or rIL-15 alone. There was also a significant increase in the splenocyte response to mitogen in the rIL-15 alone treated group, although these cells did not respond to parasite Ag in vitro. This heightened response to mitogen following rIL-15 administration has been observed previously (Seder et al., 1995 *J. Exp. Med.*, 182:1067). These observations further confirm that IL-15 can stimulate the Ag nonspecific proliferation of splenocytes in response to mitogen. However, when administered with TLA, the response is further enhanced and is driven toward Ag specificity, as indicated by the significant proliferation observed in vitro in response to parasite Ag exposure.

IL-15 has now been shown to stimulate a wide range of immune cells, including LAK cells, NK cells, B cells, and γδ T cells. It has now been found that rIL-15 can stimulate the production and proliferation of $CD8^+$ T cells that have been exposed to parasite Ag. The proliferation of $CD8^+$ T cells in response to active parasite infection has been reported (Subauste et al., 1991 *J. Immunol.*, 147:3955; Khan et al., 1994 *J. Immunol.*, 152:1856; Gazzinelli et al., 1991 *J. Immunol.*, 146:286; Brown et al., 1990 *J. Immunol.* 145:3438). However, when soluble parasite Ag alone is used for immunization, there is no apparent rise in the number of $CD8^+$ T cells. This unresponsive condition can be significantly influenced by the addition of exogenous IL-15. In the presence of both exogenous rIL-15 and parasite Ag, a near doubling in the number of $CD8^+$ T cells was observed. The presence of parasite Ag appears to be essential for this response, since rIL-15 administration alone has only a limited effect on stimulating this $CD8^+$ T cell response. This differs from previous observations on the importance both IL-12 and IL-7 to the host response to this infection. In those studies, exogenous IL-12 and IL-7 were protective when therapy was administered beginning at the time of infection. It has now been found that exogenous rIL-15 administered at the time of infection offered no protective effect, and all mice succumbed to infection at the same time as the untreated controls. A rise in the T cell population expressing the γδ TCR was observed as recently demonstrated during acute Salmonella infection (Nishimura et al., 1996 *J. Immunol.*, 156:663). However, this rise was not enhanced by the administration of IL-15. This may be due to immunization with parasite Ag rather than active infection with intact parasites. Active infection of the host with either live or attenuated parasites stimulates a strong γδ T cell response, whereas soluble parasite extract is unable to induce γδ T cell proliferation.

The ability of TLA/rIL-15 to stimulate $CD8^+$ T cells is further demonstrated by the finding that adoptive transfer of these cells into naive mice protects against subsequent challenge. T cells from nonimmunized, Ag-treated, or cytokine-treated mice failed to protect against challenge. The protective effect is mediated by $CD8^+$ and not $CD4^+$ T cells, since adoptive transfer of $CD4^+$ T cells was unable to transfer protective immunity. Further confirmation of the specificity for the $CD8^+$ T cell response is demonstrated by the cytolytic assay. The ability of *T. gondii* to stimulate a host $CD8^+$ CTL response that is parasite specific has been demonstrated previously. A marked lytic effect against macrophage-infected target cells at E:T ratios of 5:1 (32% lysis) and 10:1 (70% lysis) has been observed. This response was specific for a purified population of $CD8^+$ T cells. Thus, vaccination of mice with a combination of TLA/IL-15 is able to stimulate a significant cytolytic host $CD8^+$ T cell response against the parasite. Although $CD4^+$ lytic cells have been isolated from humans, it is not believed that $CD4^+$ T cells are an important component of this response, since no previous study in mice evaluating CTL activity has shown any lytic effect by this population.

The ability of soluble parasite Ag to stimulate $CD8^+$ cells has been observed. The major surface Ag of the parasite (p30) as well as other soluble Ags were used to stimulate a protective $CD8^+$ T cell response in both mice (Khan et al., 1988 *J. Immunol.*, 141:3600) and humans (Khan et al., 1990 *J. Clin. Invest.*, 85:1879). These $CD8^+$ T cells were cytotoxic against parasite-infected macrophages (Kasper et al., 1992 *J. Immunol.*, 148:1493) and could be adoptively transferred into naive mice to protect against parasite challenge (Khan et al., 1994 *J. Immunol.*, 152:1856). Others have also demonstrated the ability of soluble parasite Ag in the presence of the appropriate adjuvant or cytokine, such as IL-15, to stimulate a host protective immune response against parasite challenge (Denkers et al., 1993 *J. Immunol.*, 150:517).

Mice vaccinated with TLA/rIL-15 demonstrate a significant rise in the serum level of IFN-γ. The importance of IFN-γ in the host immune response to *T. gondii* is well established. The data suggest that immunization of mice with parasite Ags in combination with rIL-15 stimulates the production of IFN-γ, which is manifested by a substantial increase in the detectable levels of this cytokine circulating in the serum, as shown in Table I.

TABLE I

Serum Cytokine Concentrations of TLA/IL-15 Immunized Mice[a]

| Treatment | IFN-γ (pg/ml) | IL-10 (pg/ml) |
|---|---|---|
| Saline | Not deteated | Not detected |
| TLA | 250 ± 10 | Not detected |
| IL-15 | 500 ± 45 | Not detected |
| TLA/IL-15 | 2250 ± 50 | Not detected |

[a]Mice (n = 3/group) were immunized with IL-15 + TLA. Serum from immunized mice was collected and titers for IFN-γ were determined by ELISA.

Short term culture of the splenocytes from vaccinated mice analyzed for mRNA expression of IFN-γ did not show an increase over that in mice treated with either IL-15 or TLA alone. The inability of IL-15 to stimulate increased IFN-γ in short term culture of human PBMC from HIV-positive patients has been observed (Seder et al., 1995 *J. Exp. Med.*, 182:1067). It is possible that IL-15 is acting in synergy with another cytokine, such as IL-12, which is recognized as an important modulator of host protection against *T. gondii*.

The importance of CD8$^+$ T cells in long term immune memory to infectious agents has been observed (Lau et al., 1994 *Nature*, 369:648). Protection against acute parasite challenge for at least 1 month following vaccination with TLA/rIL-15 has now been found. CD8$^+$ T cells isolated from these mice can be stimulated in vitro with parasite Ag and exhibit a greatly enhanced CTL response against parasite-infected target cells compared with both unstimulated CD8$^+$ T cells and CD8$^+$ T cells obtained from sham-immunized control mice. It is believed that IL-15 is an important component of the host immune system involved in establishing long term CD8$^+$ T cell memory against this opportunistic agent.

Exogenous rIL-15 Administered with Parasite Antigen Protects Against Challenge Inbred BALB/CByJ mice (moderate susceptibility to infection) were immunized with parasite Ag (TLA) and rIL-15 as described. One week after the final immunization, the mice were challenged with a lethal dose of *T. gondii* tachyzoites. As shown in FIG. 2 all mice that were immunized with rIL-15 and TLA survived the lethal challenge until at least 28 days postchallenge (p.c.) when the experiment was terminated. During the postchallenge period, the only evidence of clinical illness in the vaccinated mice was the appearance of slight ruffled fur between days 10 and 13 p.c. [Immunization with either TLA or rIL-15 alone failed to provide protection]. All mice in these groups, including the nontreated control expired by day 8 p.c. To demonstrate that this effect was not mouse strain specific, rIL-15 was administered to two additional inbred mouse strains of varying susceptibility to natural infection (C57BL/6 most susceptible and A/J most resistant) Mice were treated with either rIL-IS (15 μg) or TLA alone and infected with 1×10$^4$ parasites. None of the rIL-15 or TLA alone treated mice survived beyond the control mice that received saline. Increasing the daily dose of rIL-15 (20 μg) did not further enhance protection against parasite challenge.

Figure 3:
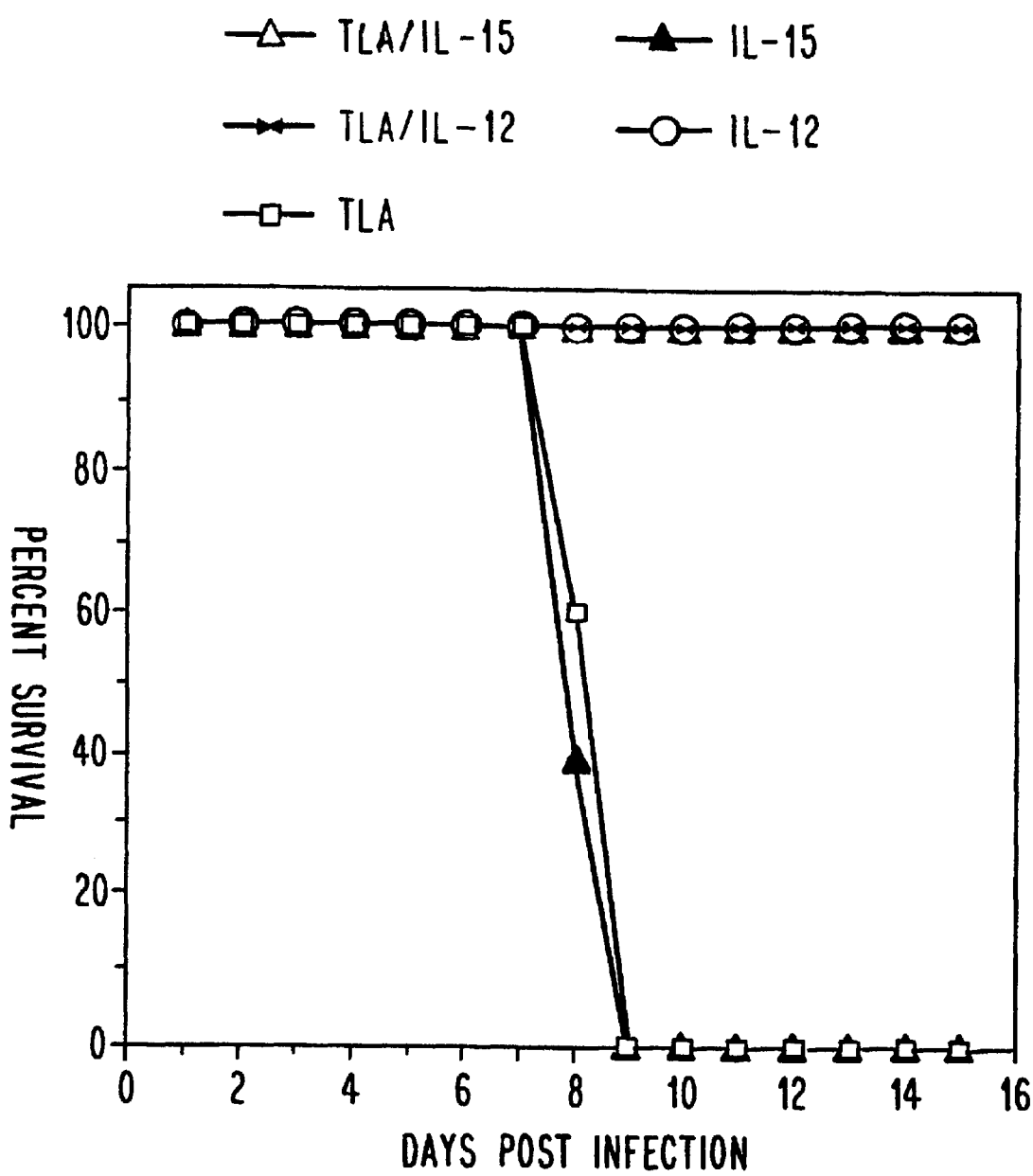
FIG. 3 is a graph showing that rIL-15, and not rIL-12, is dependent upon coadministration of TLA for protection against parasite challenge. Mice (n=6/group) were immunized with TLA and IL-15 as described above. The control animals were treated with TLA or IL-15 alone. For IL-12, mice were treated daily with IL-12 (0.33 μg) and TLA or with IL-12 alone using the same immunization schedule as that for IL-15. The mice were challenged as described in FIG. 1. The data are representative of two experiments.

The ability of rIL-15 to protect against challenge was compared with that if IL-12. As shown in FIG. 3, mice immunized with IL-12 and TLA or with IL-12 alone were protected against a lethal challenge of *T. gondii*. This differed considerably from the effect of rIL-15; treatment with this cytokine alone failed to protect, but administration of cytokine in the presence of TLA provided 100% protection against challenge.

Figure 4:
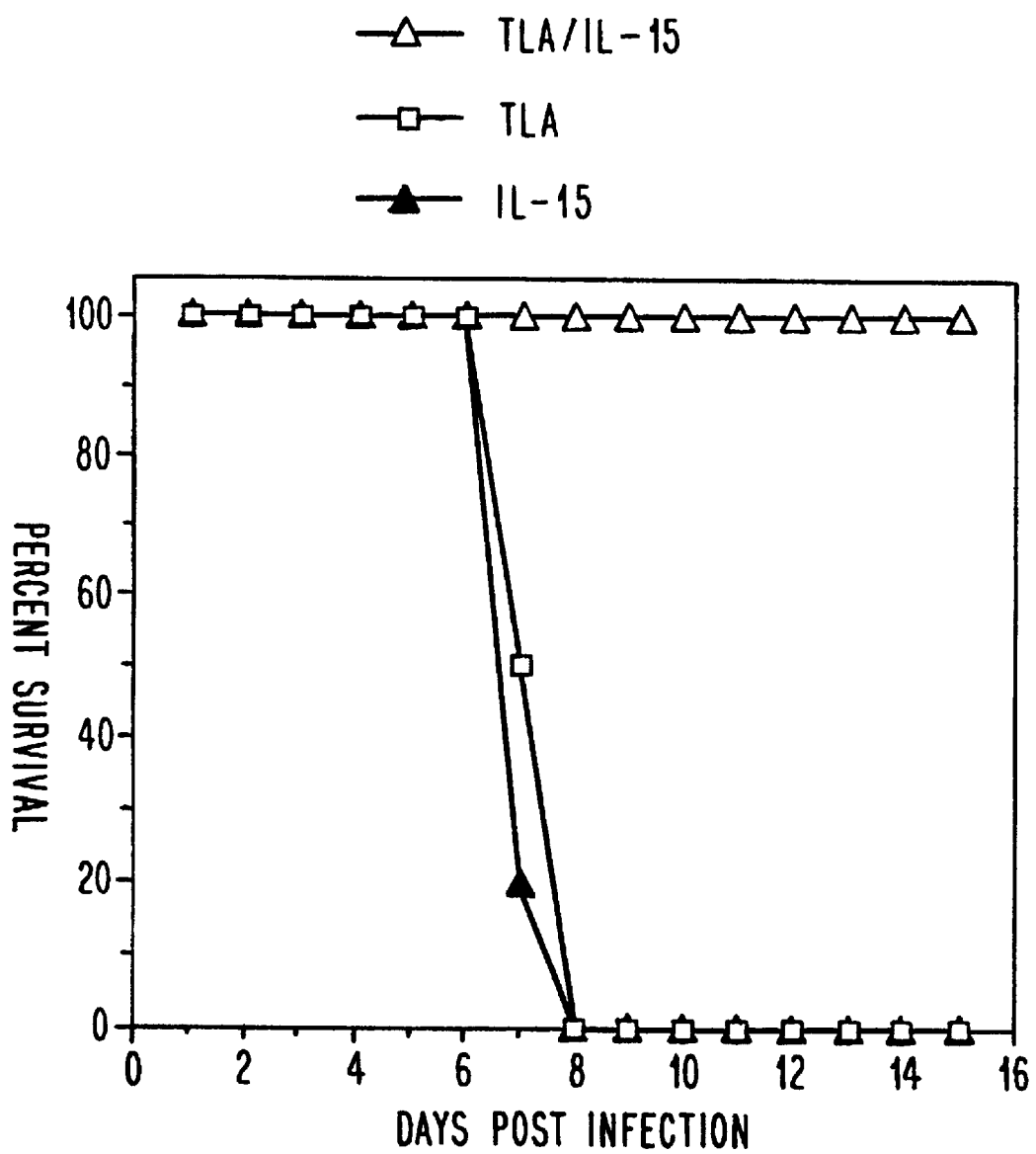
FIG. 4 is a graph showing a long term effect of vaccination with rIL-15/TLA against *T. gondii* challenge. Mice (n=6/group) were immunized with rIL-15 plus TLA, rIL-15 alone, or TLA alone as described in FIG. 1. One month after the last immunization, the mice were boosted with TLA plus IL-15, IL-15 alone, or TLA alone and challenged 1 week later with $1\times10^4$ parasites. The data are representative of two experiments.

The protective response elicited by rIL-15 and TLA persisted for at least one month postimmunization. In this experiment, mice were immunized as described above. One month after the final immunization, the mice were challenged with a lethal dose of parasites. As shown in FIG. 4, mice that received the combination of rIL-15 and TLA were fully protected. There were no overt signs of clinical infection in any of these mice. Mice that had received rIL-15 or TLA alone died within the expected time frame p.d. (days 7–9).

rIL-15 Enhances the T Cell Proliferative Response

Figure 5:
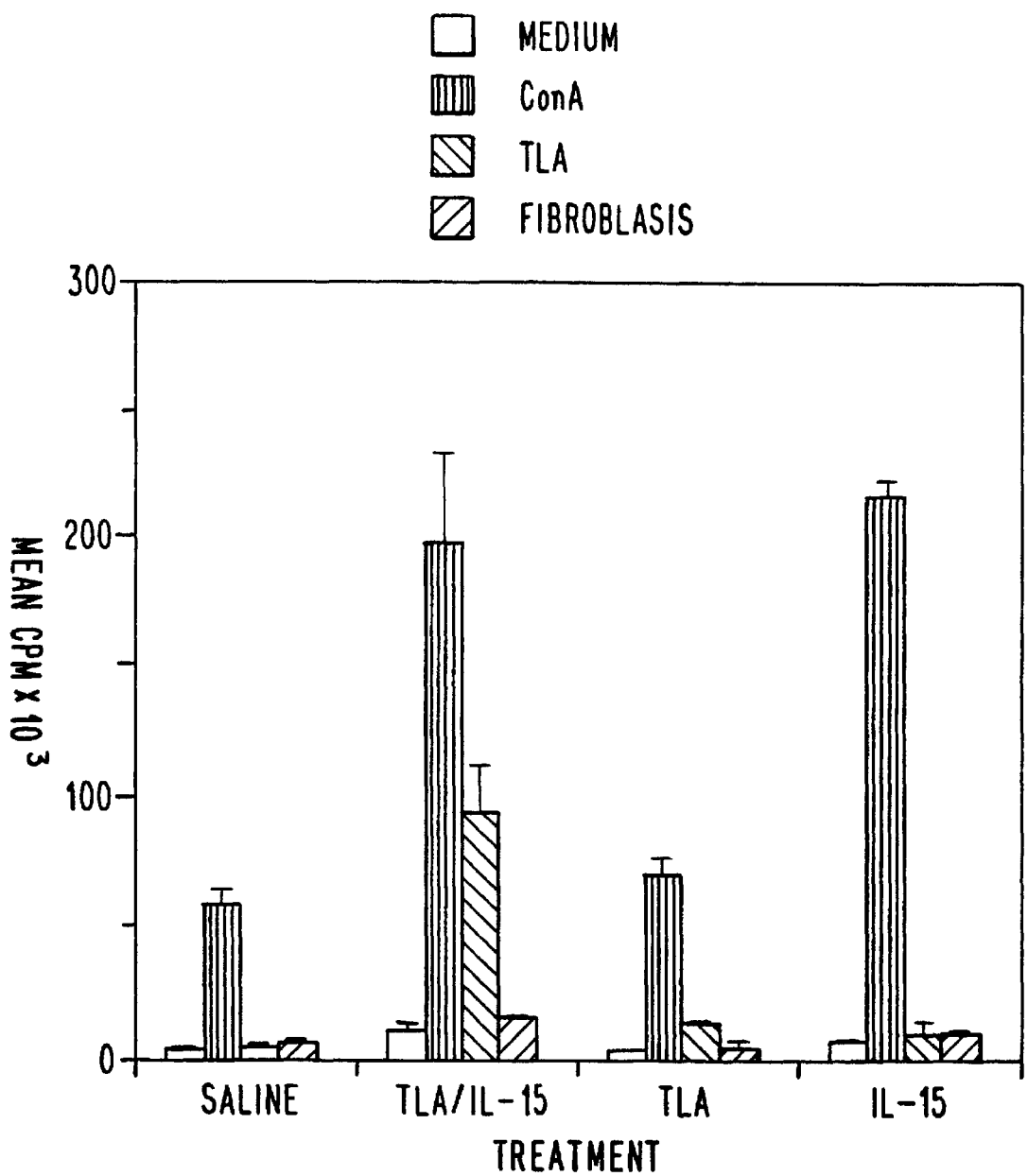
FIG. 5 is a graph showing proliferation of Ag-specific splenocytes following vaccination with TLA/rIL-15. Pooled splenocytes (n=3 mice/group) from TLA-plus IL-15, IL-15, or TLA-vaccinated mice were isolated and cultured in the presence of Con A or TLA in 96-well plates ($1 \times 10^5$ cells/well). After 72 hours, proliferation was measured by thymidine incorporation. The data are representative of two separate experiments.

A proliferation assay was performed to determine whether mice immunized with rIL-15 plus TLA responded to parasite Ag stimulation in vitro. For this experiment, mice were immunized with IL-15 plus TLA, and the splenocytes were harvested 3 days after the booster dose. Splenocytes were cultured in vitro in the presence of Con A fibroblast cell extract, or TLA. After 48 hours, proliferation was measured by [$^3$H] thymidine incorporation. As demonstrated in FIG. 5, splenocytes from mice immunized with IL-15 plus TLA proliferated in response to parasite Ag in vitro, whereas splenocytes from TLA alone immunized mice proliferated significantly less well. Mice treated with IL-15 alone or with IL-15 plus TLA showed a significantly greater Con A response than mice treated with either saline or TLA (ρ<0.02).

A phenotypic analysis of splenocyte from rIL-15-immunized mice was performed to identify the subpopulation of T cells responding to rIL-15 immunization. Mice were immunized with rIL-15, TLA, or rIL-15 plus TLA, and the splenocytes were harvested 3 days after the booster dose. The ex vivo splenocytes were stained directly for phenotypic expression using Ab staining followed by FACS analysis. As shown in Table II, rIL-15 administration alone stimulated a small increase in the number of splenocytes expressing the CD8$^+$ phenotype.

TABLE II

Phenotypic Expression of Splenocytes Following Immunization with TLA and TLA/IL-15[a]

| | CD4$^+$ | | CD8$^+$ | | γδ | |
|---|---|---|---|---|---|---|
| Treatment | % Positive | Abs. No. | % Positive | Abs. No. | % Positive | Abs. No |
| Saline | 25.40 ± 1.20 | 0.95 ± 0.06 | 15.80 ± 0.63 | 0.51 ± 0.03 | 6.8 ± 0.50 | 0.20 ± 0.02 |
| IL-15 | 27.80 ± 0.42 | 1.22 ± 0.03 | 18.15 ± 1.20 | 0.79 ± 0.09 | 10.95 ± 1.45 | 0.43 ± 0.01 |

TABLE II-continued

Phenotypic Expression of Splenocytes
Following Immunization with TLA and TLA/IL-15[a]

| Treatment | CD4+ | | CD8+ | | γδ | |
|---|---|---|---|---|---|---|
| | % Positive | Abs. No. | % Positive | Abs. No. | % Positive | Abs. No |
| TLA | 27.45 ± 0.91 | 1.19 ± 0.07 | 14.40 ± 0.42 | 0.54 ± 0.03 | 8.35 ± 0.21 | 0.30 ± 0.03 |
| IL-15 + TLA | 21.10 ± 2.40 | 1.08 ± 0.16 | 27.45 ± 0.91 | 1.35 ± 0.04 | 10.35 ± 1.35 | 0.42 ± 0.08 |

[a]Mice (n = 3/group) were immunized with IL-15 + TLA as mentioned above. Splenocytes were isolated, pooled and phenotyped for expression of either CD4+, CD8+ or γδ cells by direct immunofluorescence using FACS analysis. The data are represented as mean ± SD of two similar experiments.
Abs. No. = Absolute Number of phenotypic specific cells × $10^8$.

This was observed in both the percentage and absolute number of cells expressing this phenotype. This increase in CD8+ was further accentuated when rIL-15 was administered in the presence of TLA; there was a near doubling in the percentage and absolute number of CD8+ cells. rIL-15 plus TLA has little effect on the absolute number of T cells expressing the CD4+ phenotype. rIL-15 or TLA alone or in combination results in a near doubling of T cells expressing TCR γδ. The combination of TLA/rIL-15 does not further enhance the number or percentage of these γδ T cells These observations suggest that rIL-15 treatment increases the percentage of CD8+ T cells, and the proliferation of these cells is markedly increased when the cytokine is administered with TLA.

rIL-15 Augments the Host IFN-γ Response

It is understood that IFN-γ is the principal mediator of host protective immunity to *T. gondii* infection in mice. To determine whether rIL-15 augments this cytokine response, serum was obtained from mice 7 days following the last immunization with rIL-15/TLA and assayed from IFN-γ and IL-10. As shown in Table II, there was a considerable increase in the level of circulating IFN-γ in TLA/rIL-15-vaccinated mice. The levels of IFN-γ were elevated above the control value in mice given either rIL-15 or TLA, although they were much lower than those in mice that received the combination. A measurable level of circulating IL-10 could not be detected.

Adoptive Transfer of Protection is CD8+ T Cell Dependent

Splenocytes were isolated from TLA/rIL-15-vaccinated mice 7 days postimmunization, adoptively transferred (2×10$^7$) into naive mice, and challenged 24 hours later with a lethal dose of parasites. Splenocytes from rIL-15-plus TLA-treated mice were able to protect against parasite challenge (80% survival). In contrast, splenocytes from mice immunized with saline, rIL-15, or TLA alone did not protect naive mice against challenge, and all mice died with 9 days p.d.

Figure 6:
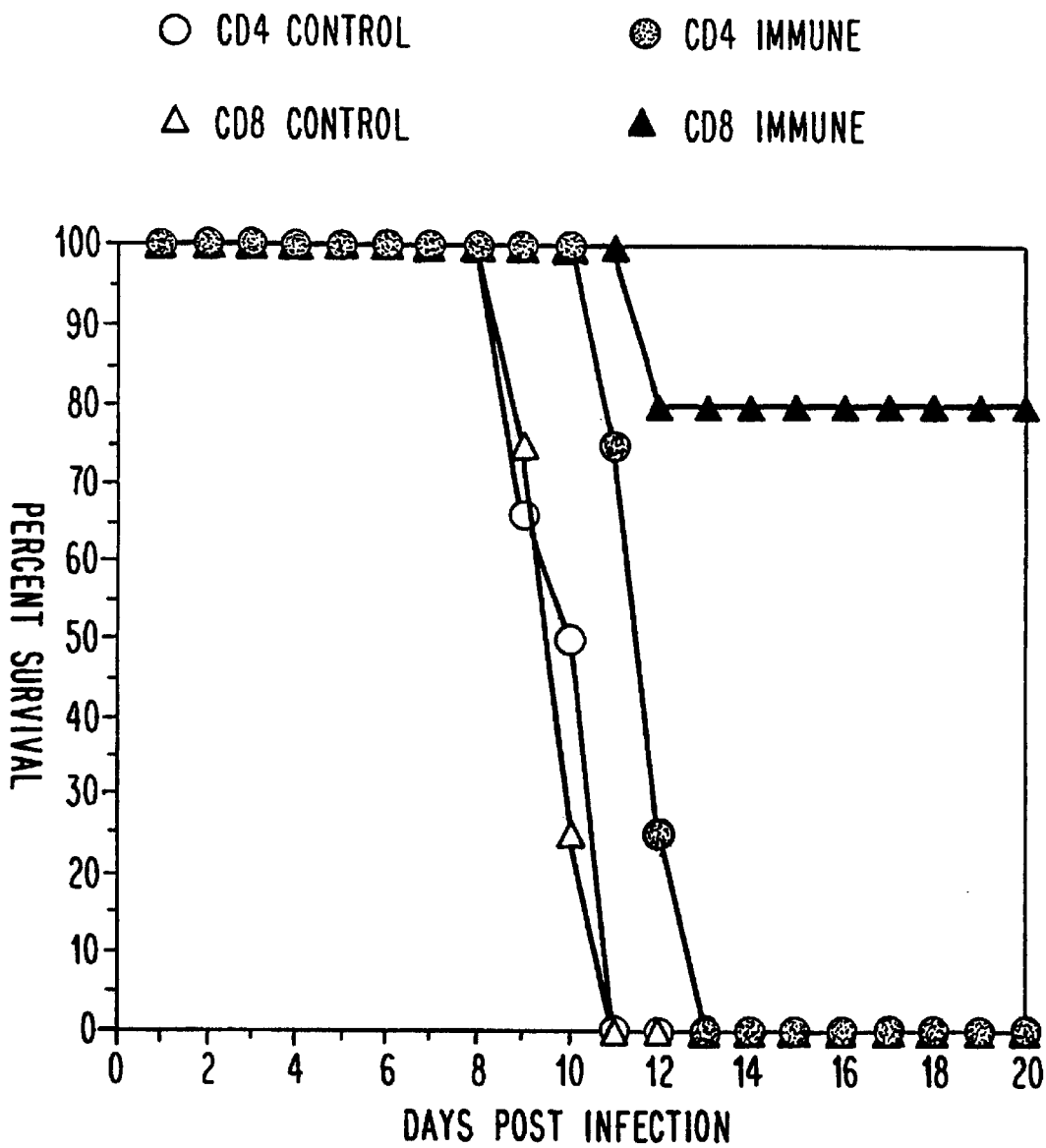
FIG. 6 is a graph showing that adoptive transfer of $CD8^+$ T cells protects against *T. gondii*. Affinity-purified $CD4^+$ or $CD8^+$ T cells were isolated from TLA/IL-15-vaccinated mice and analyzed by FACS for purity (>95% homogeneous). The purified T cells ($5 \times 10^6$) were injected by i.v. inoculation into the tail vein of naive mice (n=6/group). The next day, mice were challenged with $1 \times 10^4$ parasites, and survival was determined.

To identify the subpopulation of T cells responsible for the observed protection, splenocytes from vaccinated mice were isolated 7 days after the final immunization dose. The splenocytes were separated into CD4+ and CD8+ populations by magnetic beads. The purity of the separated population was determined by FACS (>95%), and the isolated T cells (5×10$^6$) were inoculated I.V. into naive recipient mice. The following day, the mice were challenged with a lethal dose of parasites. Mice receiving either CD4+ or CD8+ T cells from controls were dead by day 11 p.c. (FIG. 6). Mice immunized with CD4+ cells from rIL-15 plus TLA-treated mice survived longer, but all mice in that group were dead by day 13 p.c. In contrast, CD8+ T cells from immunized mice were protective (77% survival). Protection continued for at least 3 weeks p.c. until the experiment was terminated. During this time, there was no clinical evidence of illness, including ruffled fur, weight loss, or huddling.

rIL-15 Immunization Generates Memory CTL Response

Figure 7:
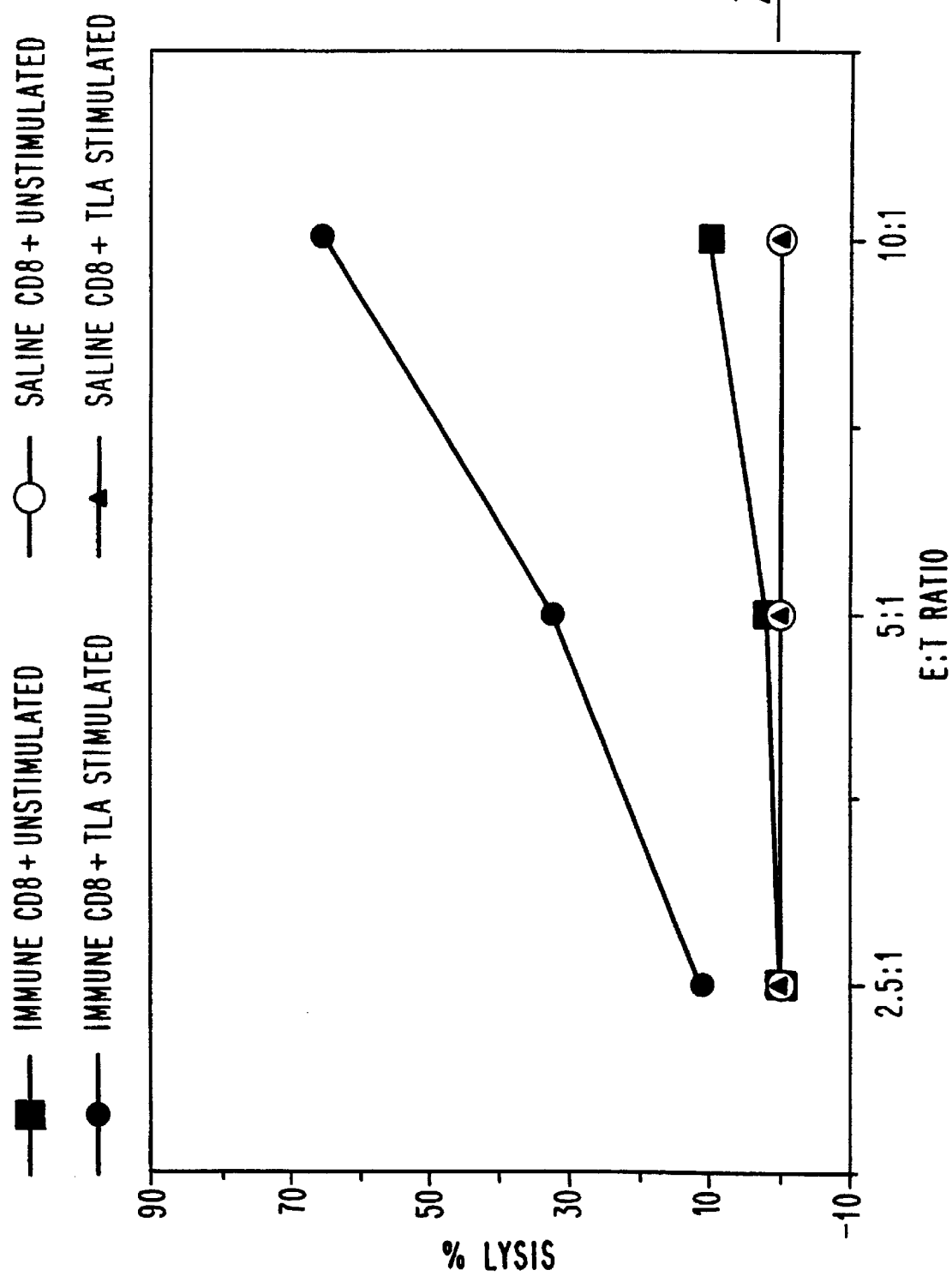
FIG. 7 is a graph showing that TLA/rIL-15 vaccination stimulates long term cytotoxic $CD8^+$ T cells. Splenocytes were isolated from mice 1 month postvaccination with TLA/rIL-15. The cells were cultured in vitro with TLA (10 μg/ml). Five days after exposure to parasite Ag, the cells were separated by density gradient on Ficoll, and the $CD8^+$ T cells purified by affinity magnetic beads (>95% homogeneous by FACS). The purified $CD8^+$ T cells were cultured with $^{51}Cr$-labeled macrophages infected with *T. gondii* at various E:T ratios. Four hours after incubation, the cytolytic activity was determined by radioisotope release into the culture supernatant. The experiment was performed twice, and the data are representative of triplicate wells.

It appeared that CD8+ T cells were an essential component of the protective response. To determine whether rIL-15 generated long term memory, an in vitro CTL assay was performed using splenocytes recovered from mice that had completed the vaccination protocol 1 month earlier. Vaccinated mice received a single booster inoculation of rIL-15/TLA, and 3 days later, the splenocytes were harvested and cultured in vitro in the presence of TLA for 5 days. The viable cells were isolated by Ficoll, and the CD8+ T cells were separated by magnetic beads. The purified CD8+ T cells were incubated with macrophage-infected targets at various E:T ratios. As shown in FIG. 7, these CD8+ T cells exhibited increase CTL activity (70% at an E:T ration of 10:1) compared with either unstimulated CD8+ T cells (10% at a 10:1 ratio) or naive CD8+ T cells (<5% lysis at a 10:1 ratio). These data suggest that the immunization with rIL-15 plus TLA may prime CD8+ CTL precursor cells, which are activated upon Ag exposure.

The following examples are provided for illustrative purposes only and are not intended to limit the invention.

EXAMPLES

Example 1

Mice and Parasites

Six- to eight-week-old female BALB/c ByJ mice were used for all studies except where indicated (The Jackson Laboratory, Bar Harbor, Me.). Other strains include similar age/sex-matched A/J or C57BL inbred mice obtained from the same source. The PLK strain of *T. gondii* (clonally derived from Mc49) was used for parasitic challenge and maintained by serial passage in a cell line of human fibroblasts (HFF) in Eagle's MEM supplemented with 10% newborn calf serum plus antibiotics. The parasites used in this experiment were <50th passage in vitro and were isolated from the monolayer by forced passage through a 27-gauge needle. For challenge experiments, mice were infected via i.p. inoculation with a 90% lethal dose (1×10$^4$) of tachyzoites.

To prepare TLA, PLK strain tachyzoites were cultured in human fibroblasts and released by forced extrusion through 27-gauge needle. Parasites were isolated from host cell debris by separation using PHA treatment and passage over a glass wool column as previously described (Kasper et al., 1983 *J. Immunol.*, 130:2407). Purified parasites were essentially free of all fibroblast contamination. The parasites were pulse sonicated eight times (18,000 Hz) at 10 second intervals at 4° C. The sonicate was centrifuged at 10,000×g for 15 minutes to remove nonsoluble Ag. The noninfectious soluble fraction (as determined by inability to infect a fibroblast monolayer) was stored at −20° C. until used. The protein concentration of the TLA preparation was determined by a commercial assay (Bio-Rad Laboratories, Cambridge, Mass.).

Fibroblast extract (as the negative control) was prepared by scraping the monolayer of a 75-mm$^2$ flask (similar to that used for parasite growth and purification), followed by forced extrusion through a 27-gauge needle. The cells were sonicated as described above, and the particulate matter was removed by centrifugation. The protein concentration was determined by commercial assay.

Example 2

Immunization with IL-15 rIL-15 was provided by Immunex Corp. (Seattle, Wash.), and IL-12 was supplied by Genetics Institute (Cambridge, Mass.). For these studies, mice were vaccinated over a 17-day period unless noted otherwise, as shown in FIG. 1. Immunization was initiated with 5 μg of TLA plus 15 μg of rIL-15 in 200 μl of PBS. For long term studies, mice were vaccinated according to the protocol in FIG. 1. Twenty-eight days after the last immunization (day 17), the mice received a single booster dose with rIL-15 and TLA. Three days later, the mice were challenged. The control mice were treated with a similar dose of rIL-15, TLA, or saline in equal volumes.

Example 3

T Cell Proliferation, Phenotyping, and Isolation

Following general anesthesia, the spleens were removed and homogenized in a petri dish, and contaminating RBC were lysed in buffer (Sigma Chemical Co., St. Louis, Mo.). The cells were suspended in RPMI 1640 (Life Technologies Institute), Gaithersburg, Md.) with 10% FCS (HyClone Laboratories, Logan, Utah) and centrifuged for 10 minutes at 500×g. Cells were cultured at a concentration of $2\times10^5$/well in 96-well flat-bottom plates on a 200-μl volume with 5 μg/ml of Con A (Sigma Chemical Co.) or 10 μg/ml of LTA. After 48 hours at 37° C., in 5% $CO_2$, [$^3$H]thymidine (0.5 μCi/well; Amersham, Arlington Heights, Ill.; specific acting 40–60 mCi/mmol) was pulsed for 8 hours to determine DNA synthesis. Pulse splenocytes were harvested on a glass filter by automated multiple sample cell harvester and dried, and incorporation of radioactive thymidine was determined by liquid scintillation.

Flow cytomeric analysis of splenocytes was performed by single color, direct immunofluorescence with the use of FACS. Briefly $1\times10^6$ splenocytes were suspended in 1 μg of FITC-labeled anti-CD4, -CD8, or -γδ TCR Ab at a 1/100 dilution (PharMingen, San Diego, Calif.) in 3% BSA/PBS. After 1 hour at 4° C., the cells were washed several times in buffer, fixed in 1% methanol-free formaldehyde, and stored in the cold for FACS analysis.

Splenocytes were separated by microbeads (Miltenyl Biotec, Auburn, Calif.) into purified $CD4^+$ t or $CD8^+$ populations using anti-CD4 or anti-CD8. The separation procedure was conducted as recommended by the manufacturer. The purity of the separated cells was >95% homology as determined by FACS analysis.

Example 4

Cytokine Detection in Serum

Serum was collected from the blood of immunized mice and tested for the presence of IFN-γ (Endogen, Cambridge, Mass.) and IL-10 (Genzyme Corp., Boston, Mass.) by ELISA according to the manufacturer's recommendations.

Example 5

Adoptive Transfer and Parasite Challenge

Inbred mice were immunized by adoptive transfer of either splenocytes or column-purified T cells. For isolation of specific T cell subsets, a magnetic bead cell sort column was used (Miltenyi Biotech, Auburn, Calif.). For this, splenocytes were isolated and prepared as described above. The cells were incubated with either anti-$CD4^+$ or anti-$CD8^+$ mAb according to the manufacturer's instructions. Following separation, the cells were analyzed for purity by FACS. All cell populations used for these studies were >95% homogeneous. Whole splenocyte or purified T cell subsets were adoptively transferred into recipient mice by i.v. tail inoculation. Twenty-four hours following the adoptive transfer of immune cells, mice were challenged with $1\times10^4$ parasites. The animals were observed daily for morbidity or mortality until the experiment was terminated.

Example 6

Cytotoxicity Assay (CTL)

A CTL assay was performed as previously described (Kasper et al., 1992 *J. Immunol.*, 148:1493). Briefly, mouse peritoneal macrophages were obtained by lavage 2 days after i.p. inoculation with 1 ml of thioglycolate. The macrophages were washed three times in PBS and dispensed at a concentration of $3\times10^4$ cells/well in U-bottom tissue culture plates in medium. Macrophages were incubated overnight and the next morning were radiolabeled with $^{51}$Cr (0.5 μCi/well; New England Nuclear Research Products, Boston, Mass.) for 3 hours at 37° C. After washing several times in PBS (or until culture supernatant contained <500 cpm), the macrophages were infected with freshly isolated cell culture grown tachyzoites at a concentration of $5\times10^4$ parasites and incubated overnight. The next morning, macrophages were washed three times in PBS and incubated with T cells at various E:T ratios in a final volume of 200 μl of culture medium. $CD8^+$ T cells were purified by magnetic beads as described above. The purity of these cells was >95% as determined by FACS analysis. Following the addition of T cells, the microtiter plates were centrifuged at 200×g for 3 minutes and incubated at 37° C. for 3 hours. One hundred-microliter samples were removed and assayed for released counts per minute by scintillation counting. The percent lysis was calculated as (mean cpm of test sample−mean cpm of spontaneous release)/(mean cpm of maximal release−mean cpm of spontaneous release)×100.

Example 7

Statistical Analysis

Statistical analysis was performed using one-way analysis of variance for lymphoproliferation studies and Fischer's exact test for the murine survival data.

What is claimed is:

1. A method of protecting an animal against *Toxoplasma gondii* infection comprising administering to an animal at the same time a noninfectious soluble fraction of a *Toxoplasma gondii* infected cell culture lysate and interleukin-15 wherein the combined effects of the cell culture lysate and interleukin-15 protect said animal against *Toxoplasma gondii* infection and wherein immunization with either said lysate or interleukin-15 alone failed to provide protection.

2. A vaccine for protection against *Toxoplasma gondii* infection in an animal comprising both a noninfectious soluble fraction of a *Toxoplasma gondii* infected cell culture lysate and interleukin-15 wherein the combined effects of the cell culture lysate and interleukin-15 protect said animal against *Toxoplasma gondii* infection and wherein immunization with either said lysate or Interleukin-15 alone failed to provide protection.

* * * * *